United States Patent
Greaves

(10) Patent No.: US 10,098,828 B2
(45) Date of Patent: Oct. 16, 2018

(54) COSMETIC METHOD FOR CONTROLLING ODORS

(71) Applicant: L'OREAL, Paris (FR)

(72) Inventor: Andrew Greaves, Magny-le-Hongre (FR)

(73) Assignee: L'OREAL, Paris (FR)

( * ) Notice: Subject to any disclaimer, the term of this patent is extended or adjusted under 35 U.S.C. 154(b) by 5 days.

(21) Appl. No.: 15/536,281

(22) PCT Filed: Dec. 15, 2015

(86) PCT No.: PCT/EP2015/079860
§ 371 (c)(1),
(2) Date: Jun. 15, 2017

(87) PCT Pub. No.: WO2016/096897
PCT Pub. Date: Jun. 23, 2016

(65) Prior Publication Data
US 2017/0360678 A1    Dec. 21, 2017

(30) Foreign Application Priority Data

Dec. 16, 2014 (FR) .................... 14 62491

(51) Int. Cl.
*A61K 8/73* (2006.01)
*A61Q 15/00* (2006.01)
*C08B 37/08* (2006.01)

(52) U.S. Cl.
CPC .............. *A61K 8/736* (2013.01); *A61Q 15/00* (2013.01); *C08B 37/003* (2013.01); *A61K 2800/81* (2013.01)

(58) Field of Classification Search
CPC ............................ A61K 2800/81; A61K 8/736
See application file for complete search history.

(56) References Cited

U.S. PATENT DOCUMENTS

| | | |
|---|---|---|
| 2003/0049290 A1 | 3/2003 | Jha et al. |
| 2004/0192646 A1 | 9/2004 | Yura et al. |
| 2005/0208309 A1 | 9/2005 | Sigrist et al. |

FOREIGN PATENT DOCUMENTS

| | | | | |
|---|---|---|---|---|
| DE | 102013202122 A | 6/2014 | | |
| KR | 20130138563 A | 12/2013 | | |
| WO | WO-02/088189 A2 | 11/2002 | | |
| WO | WO-2010076490 A2 * | 7/2010 | ............. | A61K 8/817 |
| WO | WO-2014/081391 A1 | 5/2014 | | |

\* cited by examiner

*Primary Examiner* — Kyle A Purdy
(74) *Attorney, Agent, or Firm* — Polsinelli PC

(57) ABSTRACT

The invention relates to a cosmetic method for treating human body odors. Said method includes:
(i) applying, to the skin, a composition containing a polymer (I):

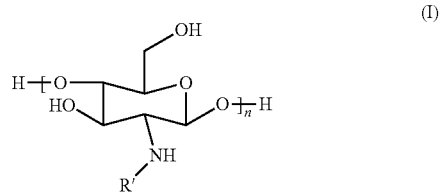

wherein R' is, separately, H or an acetyl grouping or a —CO-L-X grouping, the polymer containing at least one R'=—CO-L-X grouping,
L being a divalent hydrocarbon group containing 1 to 20 carbon atoms,
X denoting a photoactive azide or diazirine group,
and n ranging from 5 to 2000;
then (ii) exposing the skin to visible light.
The method used on the skin can also be used on materials for deodorizing malodorous environments such as shoe soles or clothing.

27 Claims, No Drawings

COSMETIC METHOD FOR CONTROLLING ODORS

CROSS REFERENCE TO RELATED APPLICATIONS

This application is a National Phase filing under 35 U.S.C. § 371 of PCT/EP2015/079860 filed on Dec. 15, 2015; and this application claims priority to Application No. 1462491 filed in France on Dec. 16, 2014 under 35 U.S.C. § 119. The entire contents of each application are hereby incorporated by reference.

The present invention relates to a process for treating odors, in particular a cosmetic process for treating human body, using a composition comprising a chitosan polymer grafted with a particular photoactive group, and exposing the treated skin to light.

In the cosmetics field, it is well known to use, in topical application, deodorant products containing active substances of antiperspirant type or of deodorant type for reducing or even preventing body odor, in particular axillary odor, which is generally unpleasant.

Eccrine or apocrine sweat generally has little odor when it is secreted. It is its degradation by bacteria via enzymatic reactions which produces malodorous compounds. Deodorant active agents thus have the function of reducing or preventing the formation of unpleasant odors.

Deodorant substances generally destroy the resident bacterial flora. Among these substances, the ones most commonly used are triclosan (2,4,4'-trichloro-2'-hydroxydiphenyl ether) and farnesol, which generally have the drawback of substantially modifying the ecology of the cutaneous flora. Furthermore, triclosan has the disadvantage of being inhibited by the presence of certain compounds, for instance nonionic surfactants, commonly used in the formulation of cosmetic compositions. Finally, the insoluble nature of triclosan in water does not allow its incorporation into essentially aqueous formulations either.

Deodorant substances may also reduce bacterial growth. Among these substances, mention may be made of transition-metal-chelating agents such as ethylenediaminetetraacetic acid (EDTA) or diethylenetriaminepentaacetic acid (DTPA). These materials have the drawback of depriving the medium of the metals necessary for bacterial growth.

There is thus still a real need to develop active compounds that have satisfactory deodorant activity and that are easy to formulate in compositions for reducing perspiration and/or odors, in particular in humans, and more particularly for combating body odor and more specifically axillary odor.

Chitosan polymers grafted with photoactive groups are described in the following documents:

The publication Kim et al., "Preparation of photo-reactive azidophenyl chitosan derivative for immobilization of growth factors", Journal of Applied Polymer Science, Volume 117 (2010), Issue 5, pages 3029-3037 describes a chitosan in which the amino groups are grafted with a 4-azidobenzoyl group.

The publication S. R. Jameela et al., "Preparation and evaluation of photo-crosslinkable chitosan as a drug delivery matrix", Journal of Applied Polymer Science, vol 86, 1873-1877 (2002) describes a chitosan in which the amino groups are grafted with a 3-azido-2-hydroxypropyl group.

The publication S. Aiba et al., "Covalent immobilization of chitosan derivatives onto polymeric film surfaces with the use of a photosensitive hetero-bifunctional crosslinking reagent". Biomaterials, 1987, 8(6):481-488 describes a chitosan in which the amino groups are grafted with a 4-azidobenzenecarboximidoyl group.

The inventors have discovered that the topical application to the skin of a chitosan polymer having amino groups grafted with photoactive groups of azide or diazirine type, combined with exposure of the treated skin to light radiation, forms a film that has a deodorant effect on the skin. The film obtained This deodorant effect exhibits good resistance to water and to rubbing. The deodorant effect of the film is also persistent with respect to water.

More specifically, a subject of the present invention is a cosmetic method for treating human body odor, in particular axillary odor, and optionally human perspiration, comprising:

(i) a step consisting in applying to the skin a composition, in particular a cosmetic composition, comprising, in a physiologically acceptable medium, a chitosan polymer in which the amino groups are grafted with photoactive groups of azide or diazirine type of formula (I) as defined below;

(ii) a step consisting in exposing the skin to light radiation, preferably for at least 5 seconds. This step can be repeated several times during the day.

The process performed according to the invention makes it possible to mask, absorb, improve and/or reduce the unpleasant odor resulting from the decomposition of human sweat. In addition, the deodorant action of the process carried out exhibits good water resistance and thus the action is persistent after washing of the treated skin. Furthermore, the film obtained, deposited on the skin, exhibits good resistance to rubbing and thus exhibits a good wear property over time.

The grafted chitosan polymer used in the process according to the invention is a polymer of formula (I):

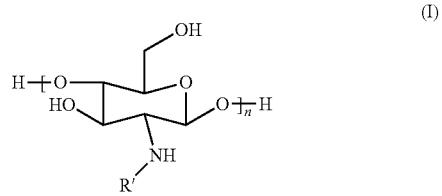

(I)

wherein R' independently represents H or an acetyl group ($CH_3C(O)-$) or a group —CO-L-X, the polymer containing at least one group R'=—CO-L-X, L being a linear, branched or cyclic, saturated or unsaturated divalent hydrocarbon-based group comprising from 1 to 20 carbon atoms, preferably from 2 to 10 carbon atoms, which may be interrupted with one or more non-adjacent heteroatoms chosen from sulfur, oxygen, or —NH—, —CO—, —CONH—, —COO—, —O—CO—N(Ra)—, in particular —O—CO—NH— or —N(Rb)—CO—N(Rc), in particular-NH—CO—NH—, groups, said divalent group possibly being substituted with one or more groups chosen from hydroxyl, amine, carboxylic acid, amide, cyano and ($C_1$-$C_4$)acylamino groups, with Ra, Rb and Rc independently denoting a hydrogen atom or a linear or branched, preferably linear, $C_1$-$C_6$ alkyl radical;

X denotes a photoactive group of azide or diazirine type;

n ranges from 5 to 2000.

Thus, the grafted chitosan (I) may also be represented according to formula (Ia):

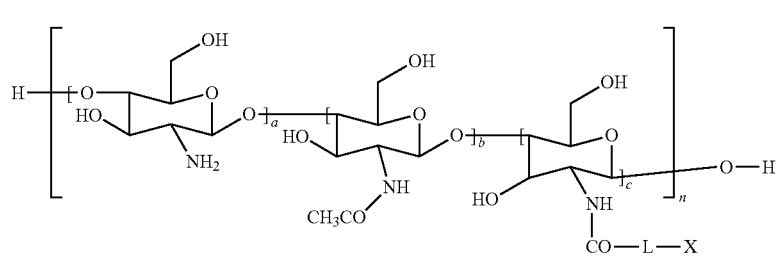
(Ia)

wherein the grafted chitosan comprises a units bearing a free amino group, b units bearing an N-acetyl amino group and c units bearing an amino group grafted with a photoactive group —CO-L-X;

b ranges from 0 to 0.5, preferably from 0.05 to 0.30, and better still from 0.1 to 0.30;

c ranges from 0.001 to 0.5, preferably from 0.01 to 0.3, and better still from 0.01 to 0.2;

and a+b+c=1,

X, L and n having the meanings described previously.

For example, when a=0.5, b=0.3 and c=0.2, this means that 50% of the amino groups are free (unsubstituted), 30% of the amino groups are acetylated and 20% of the amino groups are grafted with the group —CO-L-X, corresponding to the chitosan polymer of formula:

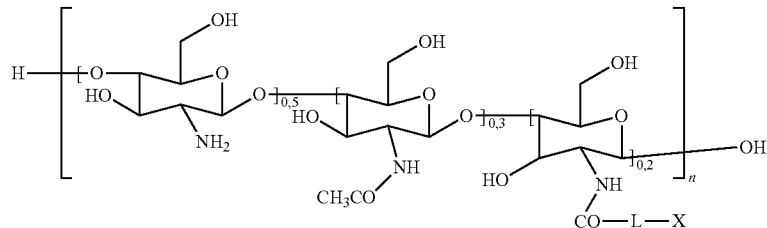

X is in particular a photoactive group such as the azide group (a) or the diazirine group (b):

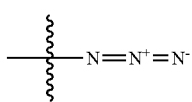
(a)

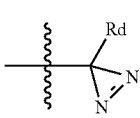
(b)

with Rd denoting H or a linear or branched, preferably linear, $C_1$-$C_6$ alkyl radical, or a $CF_3$ radical.

Preferably, the grafted chitosan has a degree of grafting with (molar content of) photoactive groups (—CO-L-X) ranging from 0.1% to 50%, preferentially ranging from 1% to 30% and more preferentially ranging from 1% to 20%.

Preferably, L is a linear, branched or cyclic, saturated or unsaturated (including aromatic) $C_1$-$C_{20}$, preferably $C_1$-$C_{10}$, divalent hydrocarbon-based radical, which may be interrupted with one or more non-adjacent heteroatoms chosen from oxygen or with one or more non-adjacent groups chosen from —NH—, —CO—, —O—CO— and —NH—CO—.

Preferably, X represents a photoactive group chosen from:

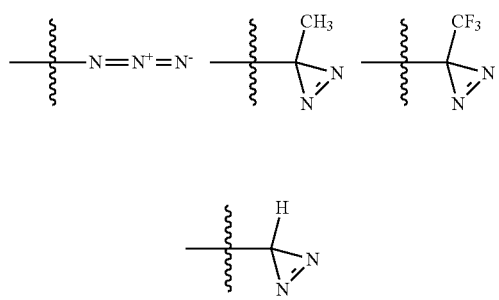

Advantageously, the grafted chitosan (I) has a degree of acetylation (—CO—$CH_3$) ranging from 0% to 50%, preferably ranging from 5% to 30%, and more preferentially ranging from 10% to 30%.

Advantageously, n ranges from 5 to 1700, preferably from 5 to 280 and more preferentially from 15 to 165.

Preferably, L denotes a divalent radical chosen from:

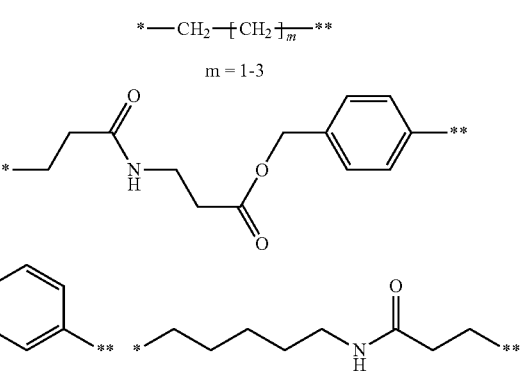

* representing the bond with the group C(O);
** representing the bond with the photoactive group X.

Preferably, the group —CO-L-X is chosen from:

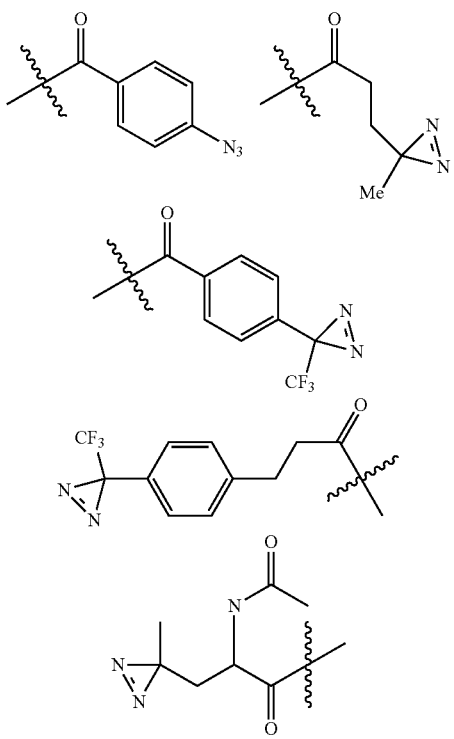

and preferentially chosen from:

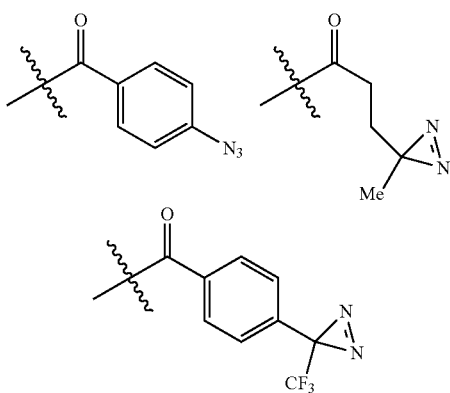

Another subject of the invention is the novel grafted polymers of formula (II):

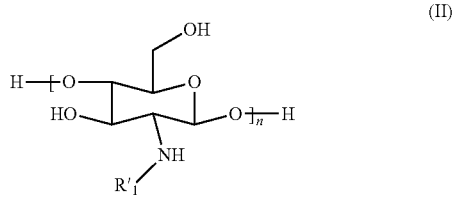

wherein R'$_1$ independently represents H or an acetyl group or a group —CO-L-X of formula (c) below:

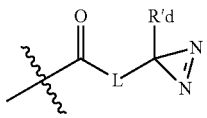

wherein:

L has the meaning described previously;

R'd denotes H or a linear or branched, preferably linear, $C_1$-$C_4$ alkyl radical, or a $CF_3$ radical;

the polymer containing at least one group —CO-L-X of formula (c), n ranges from 5 to 1700, preferably from 5 to 280 and more preferentially from 15 to 165.

Preferably, L is a linear, branched or cyclic, saturated or unsaturated (including aromatic) $C_1$-$C_{20}$ divalent hydrocarbon-based radical, which may be interrupted with one or more non-adjacent heteroatoms chosen from oxygen or with one or more non-adjacent groups chosen from —NH—, —CO—, —O—CO— and —NH—CO—.

Preferably, R'd is chosen from a hydrogen atom, a methyl radical and a $CF_3$ radical. Preferably, the grafted chitosan (II) has a degree of grafting with (molar content of) photoactive groups —CO-L-X ranging from 0.1% to 40%, preferentially ranging from 1% to 45% and more preferentially ranging from 1% to 35%.

c ranges from 0.001 to 0.4, preferably from 0.01 to 0.35, and better still from 0.01 to 0.3; with a+b+c=1.

Advantageously, the grafted chitosan (II) has a degree of acetylation ranging from 0% to 50%, preferably ranging from 5% to 45%, and more preferentially ranging from 10% to 35%.

Advantageously, n ranges from 5 to 1700, preferably from 5 to 280 and more preferentially from 15 to 165.

The grafted chitosan (II) may be a chitosan of formula (II'):

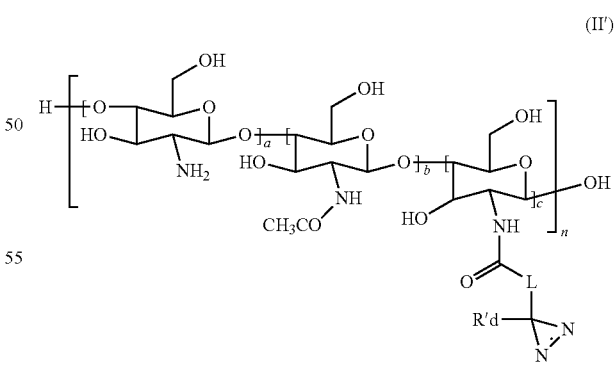

wherein a, b, c, L and R'd have the same meanings as those described previously for the compounds (Ib).

According to a first preferred embodiment of the invention, the grafted chitosan polymer (II) may be of formula (IIa) below:

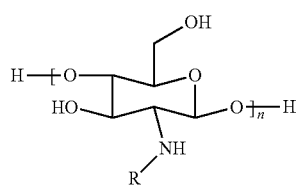

wherein R denotes H or acetyl or a group (J):

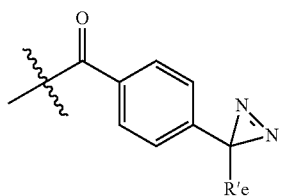

wherein R'e=CH$_3$ or CF$_3$ the polymer comprising at least one group (J). Preferably, the group J is the group:

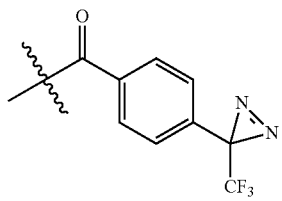 [SMILES: *C(=O)c1ccc(C2(C(F)(F)F)N=N2)cc1]

According to a second preferred embodiment of the invention, the grafted chitosan polymer (II) may be of formula (IIb) below:

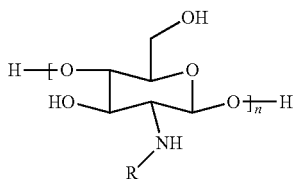

wherein R denotes H or acetyl or a group (K):

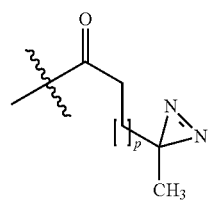

with p=1 to 3 the polymer comprising at least one group (K). Preferably, the group K is the group:

(IIa)

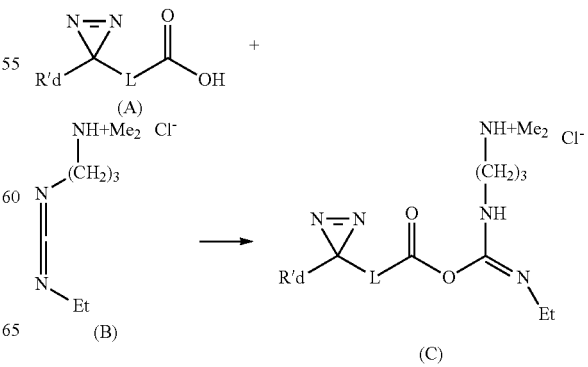

The compounds (II) can be obtained according to a first preparation method by reacting a chitosan with a carboxylic acid (A) X-L-COOH using a coupling reagent (B) so as to form an activated acid (C) and to allow the formation of an amide bond. The coupling reagent is known to those skilled in the art: use may for example be made of carbodimides such as 1-ethyl-3-(3-dimethylaminopropyl)carbodiimide hydrochloride (EDC), alkoxytriazines such as 4-(4,6-dimethoxy-1,3,5-triazin-2-yl)-4-methylmorpholinium chloride and -(hydroxyimino)acetates.

The reaction can be carried out in the presence of a second carboxylic acid activator, for example N-hydroxybenzotriazoles such as 1-hydroxybenzotriazole and N-hydroxysuccinimides such as N-hydroxysulfosuccinimide.

The reaction may take place in an aprotic or protic solvent. Preferably, the reaction takes place in water at a pH of between 4 and 9 and preferentially between 5 and 7. The reaction may be performed at a temperature of between 5 and 80° C. Preferably, the reaction takes place at ambient temperature (25° C.).

Such a coupling reaction is in particular described in the following articles: Catalytic amide formation from non-activated carboxylic acids and amines Chem. Soc. Rev., 2014, 43, 2714-2742; Evolution of amide bond formation ARKIVOC 2010 (viii) 189-250; Amide bond formation: beyond the myth of coupling reagents Chem. Soc. Rev., 2009, 38, 606-631.

In place of the carboxylic acid (A), it is possible to use an activated carboxylic acid (B) X-L-CO—O—W wherein W represents an activating group such as a group derived from N-hydroxysulfosuccinimide or from 1-hydroxybenzotriazole.

The reaction for synthesis by activation of the carboxylic acid (A) with the 1-ethyl-3-(3-dimethylaminopropyl)carbodiimide hydrochloride (B) and then grafting to the chitosan is represented diagrammatically in scheme 1 below (with simplified chitosan formula).

Scheme 1

-continued

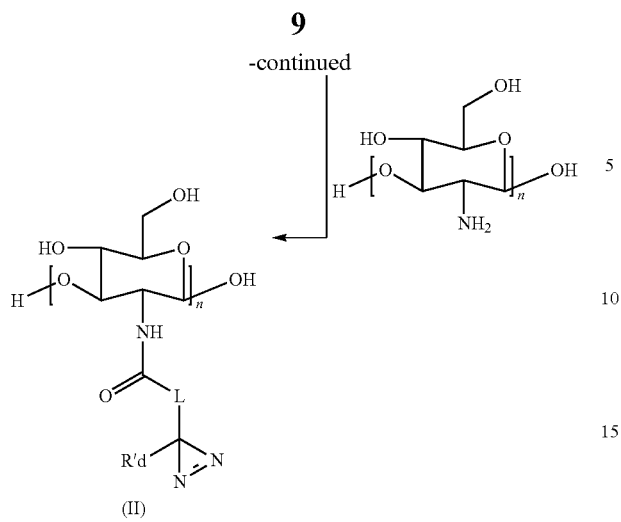

As previously indicated, a second activator such as N-hydroxysuccinimide (D) can be used according to a synthesis scheme described in scheme 2 below (with simplified chitosan formula):

Scheme 2

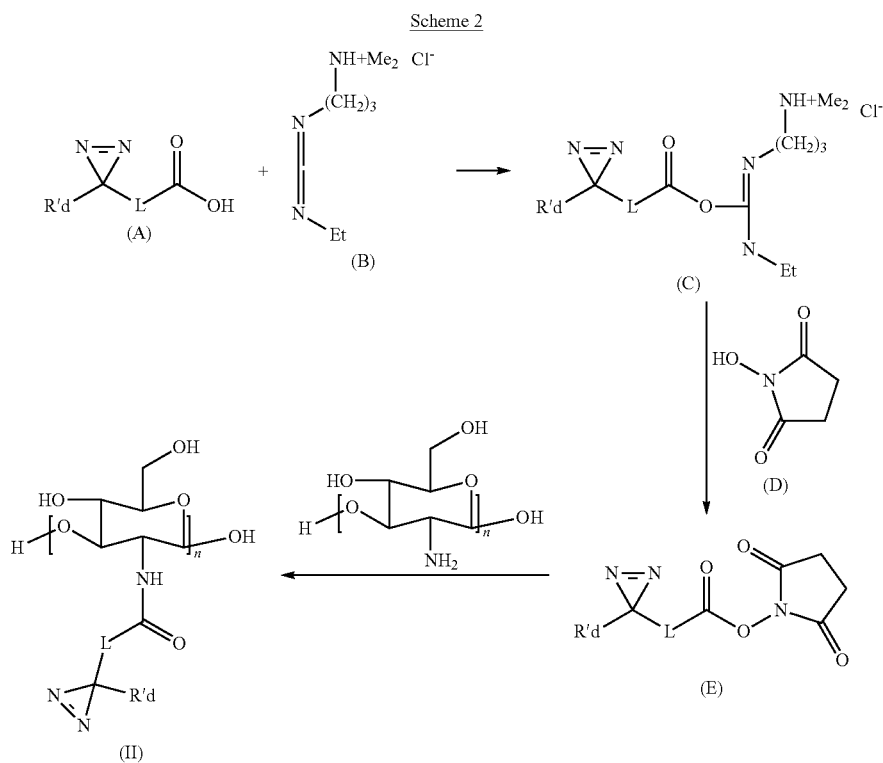

Some compounds (E) are available, such as those described in the table below. These compounds avoid the use of the coupling agent such as carbodiimides. The coupling between the chitosan and the compound (D) may be performed directly in an aprotic or protic solvent. Preferably, the reaction is performed in water at a pH of between 4 and 9 and preferably between 5 and 7. The reaction is performed at a temperature of between 5 and 80° C. Preferably, the reaction is performed at ambient temperature (25° C.).

| | |
|---|---|
| Ester of 4-[3-(trifluoromethyl)diazirin-3-yl]benzoic acid and of N-hydroxysuccinimide (from the company Toronto Research Chemicals) | 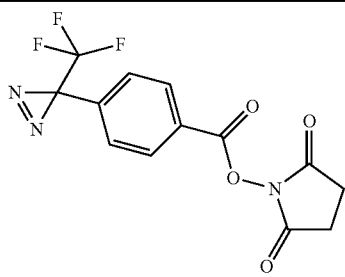 |
| Succinimidyl-diazirine (SDA from the company ThermoScientific) | 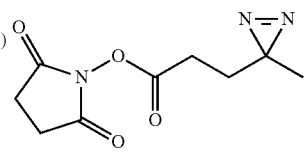 |
| Sulfo-succinimidyl-diazirine (Sulfo-SDA from the company ThermoScientific) | 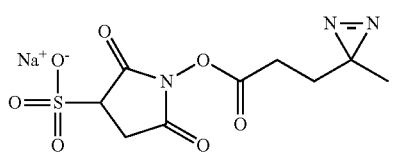 [SMILES: CC1(CCC(=O)ON2C(=O)CC(S(=O)(=O)[O-])C2=O)N=N1 ; [Na+]] |
| Succinimidyl 6-[4,4-azipentanamido]hexanoate (LC-SDA from the company ThermoScientific) | 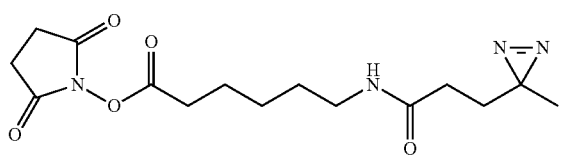 [SMILES: CC1(CCC(=O)NCCCCCC(=O)ON2C(=O)CCC2=O)N=N1] |
| Sulfosuccinimidyl 6-[4,4-azipentanamido]hexanoate (Sulfo-LC-SDA from the company ThermoScientific) | 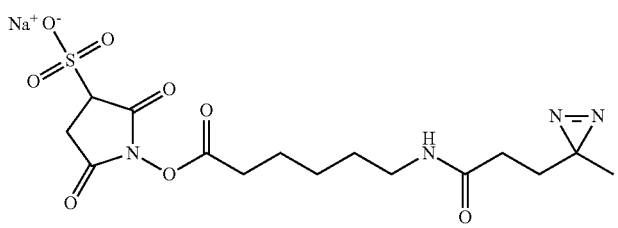 [SMILES: [Na+] ; CC1(CCC(=O)NCCCCCC(=O)ON2C(=O)CC(S(=O)(=O)[O-])C2=O)N=N1] |

Some of the non-activated carboxylic acids (A) comprising a photoreactive group are commercially available, such as those mentioned in the table below:

| | |
|---|---|
| 4-[3-(Trifluoromethyl)-3H-diazirin-3-yl]benzoic acid from the company TCI | 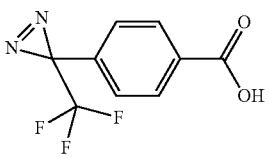 [SMILES: O=C(O)c1ccc(C2(C(F)(F)F)N=N2)cc1] |
| α-(acetylamino)-3-methyl-3H-diazirine-3-propanoic acid from the company ChemStep | 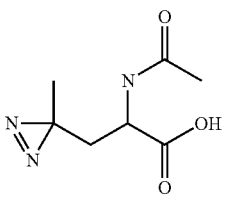 |
| 4-(3-methyl-3H-diazirin-3-yl)butanoic acid from the company FineChemie & Pharma | 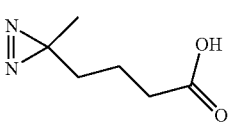 |

| | |
|---|---|
| 4-[3-(trifluoromethyl)-3H-diazirin-3-yl]benzenepropanoic acid from the company Dalton Pharma | 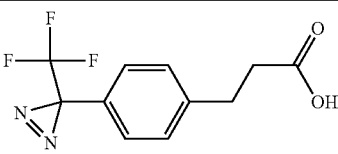 |

A subject of the invention is also a composition comprising, in a physiologically acceptable medium, a grafted polysaccharide (II) or (IIa) or (IIb) as defined previously.

The composition used according to the invention is generally suitable for topical application to the skin and thus generally comprises a physiologically acceptable medium, i.e. a medium that is compatible with the skin and/or its integuments. It is preferably a cosmetically acceptable medium, i.e. a medium which has a pleasant color, odor and feel and which does not cause any unacceptable discomfort (stinging, tautness or redness) liable to discourage the consumer from using this composition.

The grafted chitosan (I) or (Ia) or (II) or (IIa) or (IIb) may be present in the composition according to the invention in a content ranging from 0.1% to 10% by weight, preferably ranging from 0.5% to 10% by weight, preferentially ranging from 1% to 8% by weight and more preferentially ranging from 1% to 6% by weight relative to the total weight of the composition.

The composition according to the invention may be in all galenical forms conventionally used for topical application and in particular in the form of dispersions of aqueous gel or lotion type, emulsions of liquid or semi-liquid consistency of the milk type, obtained by dispersing a fatty phase in an aqueous phase (O/W) or vice versa (W/O), or suspensions or emulsions of soft, semi-solid or solid consistency of the cream or gel type, or alternatively multiple emulsions (W/O/W or O/W/O), microemulsions, vesicular dispersions of ionic and/or nonionic type, or wax/aqueous phase dispersions. These compositions are prepared according to the usual methods.

According to one preferred embodiment of the invention, the composition is in the form of an O/W emulsion or an aqueous gel.

Advantageously, the composition used according to the invention comprises water, in particular in a content which can range from 10% to 99% by weight and preferably ranging from 50% to 99% by weight, relative to the total weight of the composition.

The composition used according to the invention may also contain one or more adjuvants commonly used in the cosmetics field, such as emulsifiers, preservatives, sequestering agents, fragrances, thickeners, oils, waxes or film-forming polymers.

Needless to say, those skilled in the art will take care to select this or these optional additional compounds, and/or the amount thereof, such that the antiwrinkle properties of the composition according to the invention are not, or are not substantially, adversely affected by the envisaged addition.

Advantageously, for the process according to the invention, it is possible to apply 0.01 to 0.5 g of cosmetic composition comprising the grafted chitosan polymer, in particular 0.05 to 0.1 g of composition, per cm$^2$ of skin.

The process according to the invention also comprises a step consisting in exposing the skin to light radiation preferably having a wavelength of between 360 and 600 nm.

It is possible to perform this step consisting in applying light radiation after or at the same time as (simultaneously with) the step consisting in applying the composition comprising the grafted chitosan polymer.

Preferentially, in a first step, the composition comprising the grafted chitosan polymer is applied to the skin, and then, in a second step, light radiation is applied to the skin.

It is possible to perform a step of rinsing, for example with water, the skin between each step of the process.

Preferably, the light radiation used in the process according to the invention has a wavelength of between 400 and 480 nm.

The light radiation preferably has a flux (amount of energy per unit surface area) ranging from 3 to 100 J/cm$^2$ and preferably ranging from 3 to 10 J/cm$^2$.

The light radiation may be continuous or non-continuous light.

The light radiation may be natural light (daylight).

The light radiation may be generated by a device, such as arc lamps such as xenon lamps and mercury lamps; fluorescent lamps; incandescent lamps such as halogen lamps; LEDs and lasers.

Mention may be made in particular of the goLITE BLUs from the company Philips, the lamp Energylight HF 3319/01 from the company Philips, the lamps Dayvia White and Messa from the company Solvital, the lamp Lumino Plus from the company Lanaform, the lamp Medibeam from the company Medibeam, the lamp M-LED 01 from the company Meimed, the lamp Lifemax Light Pod from the company Lifemax, the lamp Lite-Pad from the company Reicorp, and the lamp Camag Box 3 (4×8 W) from the company Camag.

The exposure time of the treated skin to the light radiation provided by a device is preferably at least 5 seconds. Preferably, this exposure time can range from 10 seconds to 15 minutes, in particular between 15 seconds and 10 minutes, even better still between 20 seconds and 5 minutes, regardless of the order of the steps (one before the other or simultaneous).

By way of example, in the case of simultaneous application of the light radiation provided by a device and of the composition comprising the grafted chitosan polymer, the light-exposure time may advantageously range from 5 seconds to 15 minutes. It is possible to perform rinsing of the composition.

By way of example, in the case of application of the composition according to the invention followed by exposure to light radiation provided by a device, the light-exposure time may advantageously be between 5 seconds and 15 minutes. It is possible to leave the composition used according to the invention in place for a period of 1 second to 3 hours, before performing the step of applying the light radiation. It is possible to perform rinsing of the composition, after the step of exposure to light radiation.

The exposure time of the treated skin to daylight as light radiation is preferably at least 30 seconds. Preferably, this exposure time may range from 30 seconds to 1 hour, in particular between 30 seconds and 30 minutes, even better still between 1 minute and 15 minutes, regardless of the order of the steps (one before the other or simultaneous).

By way of example, in the case of simultaneous application of daylight and of the composition comprising the grafted chitosan, the light-exposure time may advantageously range from 3 minutes to 12 hours. It is possible to perform rinsing of the composition.

By way of example, in the case of application of the composition comprising the grafted chitosan, followed by exposure to daylight, the light-exposure time may advantageously be between 3 minutes and 12 hours. It is possible to leave the composition according to the invention in place for a period of 1 second to 3 hours, before performing the step of exposure to light radiation.

It is possible to perform rinsing of the composition, after the step of exposure to light radiation, but this is not obligatory.

The step of exposure to light radiation may be repeated several times during the day.

The application of the cosmetic composition used according to the invention is performed according to the usual techniques, for example by application (in particular of creams, gels, sera or lotions) to the skin intended to be treated, in particular the skin of the armpits or the feet.

The process applied to the skin may also be applied to materials intended for deodorizing malodorous environments.

Thus, a subject of the invention is also a process for deodorizing the feet and/or the shoes, consisting in placing in a shoe a sole of which the surface has been treated by applying to said surface a composition comprising a grafted chitosan (I) as described previously, and then exposing the treated surface to light radiation, preferably for at least 5 seconds.

The sole may be made of cork, of rubber or of leather.

A subject of the invention is also a process for deodorizing the body (or part of the body), consisting in clothing the body (or part of the body) with clothing made of textile fabric of which the surface has been treated by applying to the surface of the textile a composition comprising a grafted chitosan (I) as described previously, and then exposing the treated surface to light radiation, preferably for at least 5 seconds.

The part of the body may be the feet and the item of textile clothing may be socks, stockings or tights. The part of the body may be the chest and the item of textile clothing a T-shirt.

A subject of the invention is also a process for deodorizing the feet, consisting in clothing the feet with an item of clothing for the feet made of textile fabric, in particular in the form of socks or stockings or tights, treated by applying to said textile fabric a composition comprising a grafted chitosan (I) as described previously, and then exposing the treated textile fabric to light radiation, preferably for at least 5 seconds.

The textile of the clothing may be cotton, wool, silk, linen, polyamide, polyester, polylactic acid, chloride fibers, polyacrylonitrile, elastane, aramid, polybenzimidazole, polypropylene, polyethylene, polyphenol, polyurea, polyurethane, or mixtures thereof. The treatment is preferably applied to the textile before the production of the clothing with said treated textile.

The treatment of soles or of textile can be performed with an aqueous composition containing the grafted chitosan polymer.

The radiation-exposure conditions described previously apply to these various processes.

The invention will now be described with reference to the following examples, which are given as nonlimiting illustrations. The contents are expressed as weight percentages.

SYNTHESIS EXAMPLE 1 (POLYMER 1)

Chitosan 18%-Functionalized with a diazirine group

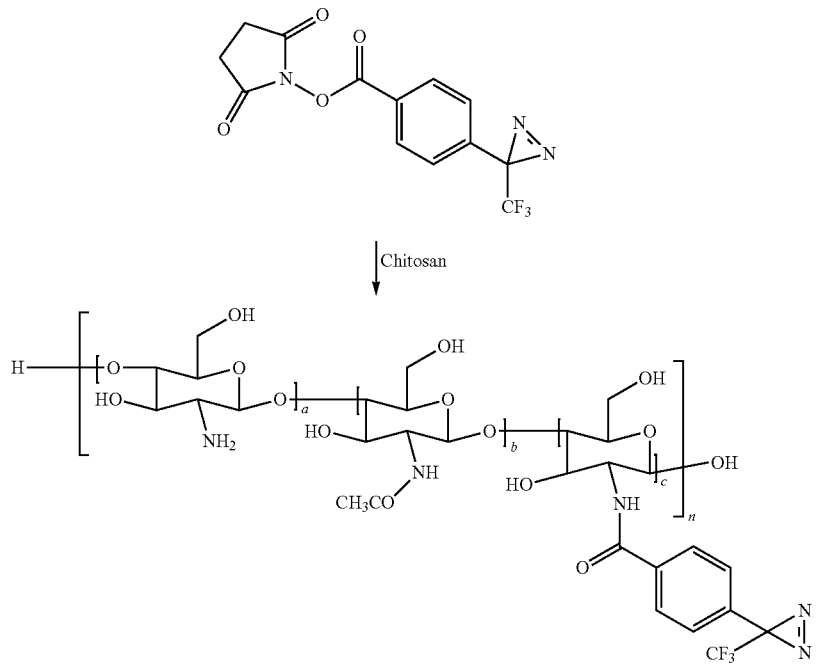

with a=0.52; b=0.30; c=0.18 n being such that the ungrafted chitosan has a molecular weight Mn=28 000 daltons 5 g of chitosan (Zenvivo® Protect from Clariant with a degree of acetylation (mol %)=30% and a molecular weight Mn=28 kDa) were dissolved in 250 g of an aqueous solution of acetic acid at 1% by weight, in a round-bottomed flask protected from light. A solution of 9 g of ester of 4-[3-(trifluoromethyl) diazirin-3-yl]benzoic acid and of N-hydroxysuccinimide in 81 ml of dioxane was then added. After 10 minutes of stirring, the pH was adjusted to 5 with an aqueous sodium bicarbonate solution (2M). The solution was stirred at ambient temperature (25° C.) for 4 days. The reaction mixture was then introduced into a dialysis tube (Spectra/Por Dialysis Membrane MWCO 3500; NFW 54 mm, Diam. 34 mm, vol./length 9.3 ml/cm; Spectrumlabs.com ref 132725) and dialyzed in 2 liters of water for 4 days, replacing the water twice a day. The aqueous solution was lyophilized to give a fibrous solid yellow product. This recovered solid was washed at ambient temperature in a brown flask using acetone (once with 1 liter then twice with 500 ml).

The solid residue was then filtered off for 5 minutes and then dried under vacuum at ambient temperature for 12 hours. 5.8 g of a beige-colored solid product (powder) were thus obtained.

The product was stored in an amber-colored flask at −20° C.

The 1H NMR analysis in deuterated water: 18% grafting

SYNTHESIS EXAMPLE 2 (POLYMER 2)

Chitosan 1%-Functionalized with a Diazirine Group with a=0.69; b=0.30; c=0.01 n being such that the ungrafted chitosan has a molecular weight Mn=28 000 daltons 0.5 g of chitosan (Zenvivo® Protect from Clariant with a degree of acetylation=30% and a molecular weight Mn=28 kDa) was dissolved in 25 ml of an aqueous solution of acetic acid at 1% by weight in a round-bottomed flask protected from light. The solution was stirred and then a mixture of 10 ml of ethanol, 0.38 g of 4-[3-(trifluoromethyl)diazirin-3-yl]benzoic acid and 0.54 g of 1-ethyl-3-(3-dimethylaminopropyl)carbodiimide hydrochloride (EDC) was added. The reaction mixture was stirred at 40° C. for 3 hours, cooled, then introduced into a dialysis tube (Spectra/Por Dialysis Membrane MWCO 3500; NFW 54 mm, Diam. 34 mm, vol/length 9.3 ml/cm; Spectrumlabs.com ref 132725) and dialyzed in 5 liters of water for 72 hours, replacing the water 6 times during this dialysis operation. The solution was then lyophilized so as to obtain a fibrous solid pale yellow product. This recovered solid was washed at ambient temperature using acetone, for 2 hours (100 ml per wash, 3 washes being performed). The grafted product remains insoluble in acetone.

The solid residue was then filtered off for a few minutes and then dried under vacuum at ambient temperature for 12 hours. 385 mg of a beige-colored solid product (powder) were thus obtained.

The product was stored in an amber-colored flask at −20° C.

The 1H NMR analysis in deuterated water: 1% grafting

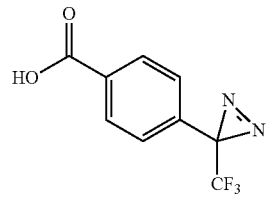

Chitosan, EDC

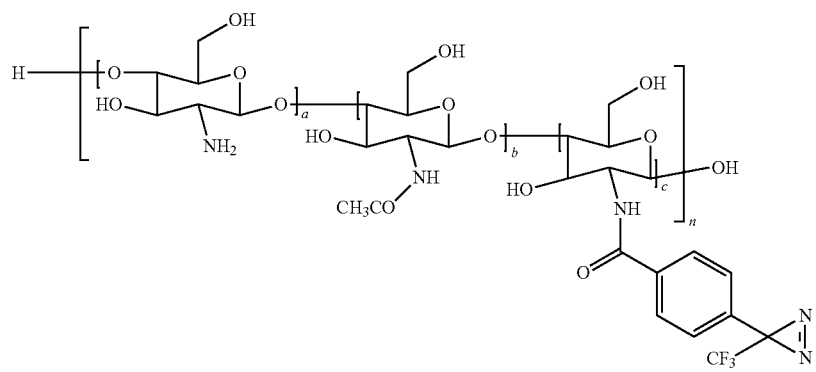

SYNTHESIS EXAMPLE 3 (POLYMER 3)

Chitosan 5%-Functionalized with a Diazirine Group

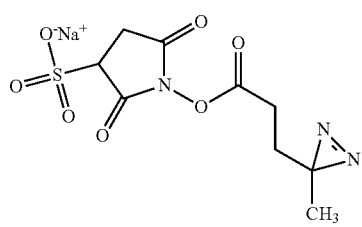

↓ Chitosan

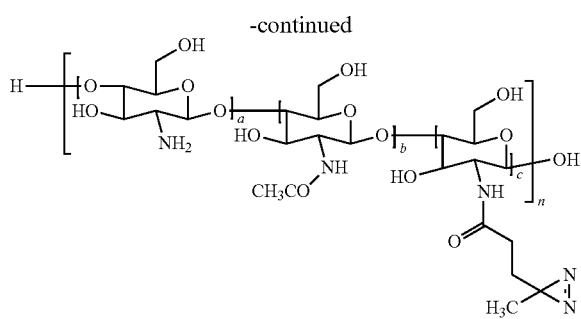

with a=0.65; b=0.30; c=0.05
n being such that the ungrafted chitosan has a molecular weight Mn=28 000 daltons.

200 mg of chitosan (Zenvivo® Protect from Clariant with a degree of acetylation (mol %)=30% and a molecular weight Mn=28 kDa) were dissolved in 4.2 ml of distilled water in a round-bottomed flask covered with aluminum foil so as to prevent exposure to light. 50 mg of succinimidyl 4,4'-azipentanoate (sulfo-SDA from the company Thermo-Scientific) was added, with stirring at temperature (5° C.). The reaction mixture was stirred for 24 h while allowing the temperature to increase to 22° C. and keeping the pH between 4 and 5 by adding an aqueous acetic acid solution (1% by weight). The reaction mixture was then introduced into a dialysis tube (MWCO 3 kDa) and dialyzed in 5 liters of osmosed water for 48 hours, the water being replaced 6 times during this dialysis operation. The solution was lyophilized so as to obtain a fibrous solid yellow product (187 mg).

The product was stored in an amber-colored flask at −20° C.

The 1H NMR analysis in deuterated water: 5% grafting

SYNTHESIS EXAMPLE 4 (POLYMER 4)

Chitosan 9%-Functionalized with an Azide Group

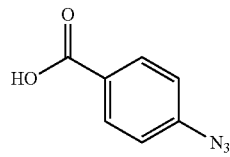

↓ Chitosan, EDC

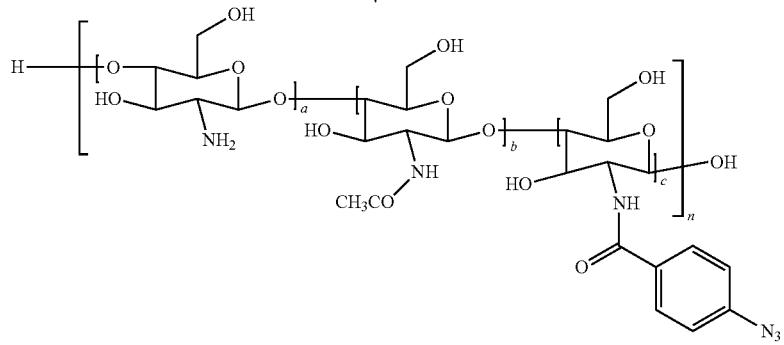

with a=0.73; b=0.18; c=0.09
n being such that the ungrafted chitosan has a molecular weight Mn=28 000 daltons 0.5 g of chitosan (Zenvivo® Protect from Clariant with a degree of acetylation (mol %)=30% and a molecular weight Mn=28 kDa) was dissolved in 25 ml of an aqueous solution of acetic acid at 1% by weight in a round-bottomed flask protected from light. The solution was stirred and then a mixture of 5 ml of ethanol, 0.38 g of 4-azidobenzoic acid and 0.54 g of 1-ethyl-3-(3-dimethylaminopropyl)carbodiimide hydrochloride (EDC) was added. The reaction mixture was stirred at 40° C. for 3 hours, cooled, and then introduced into a dialysis tube (MWCO 3 kDa) and dialyzed in 5 liters of water for 48 hours, the water being replaced 4 times during this dialysis operation. The solution was then lyophilized so as to obtain a fibrous solid pale yellow product. This recovered solid was washed at ambient temperature using acetone, for 2 hours (100 ml per wash, 3 washes being performed). The grafted product remains insoluble in acetone.

The solid residue was then filtered off for a few minutes and then dried under vacuum at ambient temperature for 12 hours. 360 mg of a beige-colored solid product (powder) were thus obtained.

The product was stored in an amber-colored flask at −20° C.

The 1H NMR analysis in deuterated water: 9% grafting

SYNTHESIS EXAMPLE 5 (POLYMER 5)

Chitosan 4%-Functionalized with an Azide Group

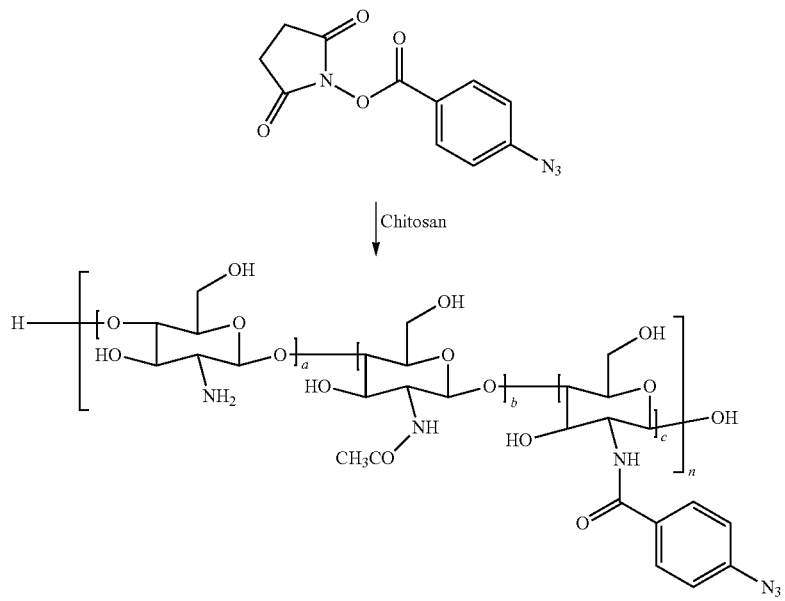

with a=0.66; b=0.3; c=0.04 n being such that the ungrafted chitosan has a molecular weight Mn=28 000 daltons.

250 g of chitosan (Zenvivo® Protect from Clariant with a degree of acetylation (mol %)=30% and a molecular weight Mn=28 kDa) was dissolved in 25 ml of an aqueous solution of acetic acid at 1% by weight, in a round-bottomed flask protected from light. A solution of 50 mg of 1-{[(4-azidophenyl)carbonyl]oxy}pyrrolidine-2,5-dione in 3 ml of dioxane was then added. After 10 minutes of stirring, the pH was adjusted to 5 with an aqueous sodium hydroxide solution (1M). The reaction mixture was stirred at ambient temperature for 18 hours. The reaction mixture was then filtered and then the filtrate was introduced into a dialysis tube (Spectra/Por Dialysis Membrane MWCO 3500; NFW 54 mm, Diam. 34 mm, vol./length 9.3 ml/cm; Spectrumlabs.com ref 132725) and dialyzed in 2 liters of water for 3 hours, with the water being replaced 3 times. The solution was lyophilized to give a fibrous solid yellow product. This recovered solid was washed at ambient temperature in a brown flask using acetone (once with 1 liter then twice with 500 ml). The grafted product remains insoluble in acetone.

The solid residue was then filtered off for 5 minutes and then dried under vacuum at ambient temperature for 12 hours. 120 g of a beige-colored solid product (powder) was thus obtained.

The product was stored in an amber-colored flask at −20° C.

The 1H NMR analysis in deuterated water: 4% grafting

EXAMPLES 1 To 8

Demonstration of the Deodorant Effect of the Polymers Used According to the Invention The following compositions were prepared:

Composition 1: water

Composition 2: aqueous solution containing 5% by weight of AM of chitosan Zenvivo Protect from Clariant Composition 3: aqueous solution containing 5% by weight of AM of polymer 1

Composition 4: aqueous solution containing 5% by weight of AM of polymer 2

Composition 5: aqueous solution containing 5% by weight of AM of polymer 3

Composition 6: aqueous solution containing 5% by weight of AM of polymer 4

Composition 7: aqueous solution containing 5% by weight of AM of polymer 5

Preparation of the Substrate

Pieces of human stratum corneum are stuck onto adhesive tape (reference 1526886 from the company Office Depot), taking care that the external surface of the stratum corneum is not in contact directly with the adhesive tape. The substrates are then cut into strips approximately 2 cm long and 1 cm wide and used with the adhesive tape in the lower part and the outer surface of the stratum corneum in the upper part.

The outer surface of the stratum corneum was cleaned with a wipe impregnated with ethanol.

Application of the compositions:

EXAMPLES 1 To 3

100 µl of each of the compositions 1 to 3 were applied, respectively, to the surface of the stratum corneum and left to stand for 10 minutes, and were then rinsed off with 13 ml of aqueous 0.9 M NaCl solution, and the surface was then wiped with absorbent paper.

EXAMPLE 4

100 µl of composition 3 were applied to the surface of the stratum corneum and left on for 5 minutes, and then the surface was irradiated with an Oriel sun simulator device from the company Oriel-Lott for 5 minutes. Rinsing was then carried out with 13 ml of an aqueous 0.9M NaCl solution and the service was then wiped with absorbent paper.

The treated strips of stratum corneum were cut into small pieces about 3 mm×3 mm in size and placed in a plastic flask. 100 µl of human sweat were added, and the flask was closed and shaken. The flask was then placed in an incubator for 24 hours (37° C., 5% $CO_2$).

A panel of 4 people then evaluated the sweat odor perceived on opening each flask (examples 1 to 4).

The water resistance of the treated stratum corneum samples was then measured by performing a washing/rinsing cycle by grasping the pieces of stratum corneum with forceps, dipping them for 5 seconds in 10 ml of aqueous solution containing 15% by weight of sodium lauryl ether sulfate and then rinsing them by dipping them in 20 ml of distilled water for 10 seconds, and repeating this washing/rinsing cycle 4 times. The pieces of stratum corneum thus washed were placed in a plastic flask, and 100 µl of human sweat were added. The closed flask was placed in an incubator for 24 hours (37° C., 5% $CO_2$).

A panel of 5 people then evaluated the sweat odor perceived on opening each flask (examples 1a to 4a).

Another washing/rinsing cycle was recommenced and the sweat odor perceived was evaluated (examples 1b to 4b).

The following results were obtained:

The following results were obtained:

| example | Control evaluation A | Control evaluation B | Control evaluation C | Control evaluation D | mean |
|---|---|---|---|---|---|
| 1 (without washing | 5 | 5 | 5 | 5 | 5 |
| 1a (1 washing cycle) | 5 | 5 | 4 | 5 | 4.75 |
| 1b (2 washing cycles) | 5 | 3 | 3 | 3 | 3.5 |
| 2 (without washing) | 1 | 4 | 2 | 1 | 2 |
| 2a (1 washing cycle) | 3 | 3 | 5 | 3 | 3.5 |
| 2b (2 washing cycles) | 4 | 2 | 1 | 3 | 2.5 |
| 3 (without washing) | 0 | 1 | 0 | 2 | 0.75 |
| 3a (1 washing cycle) | 1 | 1 | 1 | 4 | 1.75 |
| 3b (2 washing cycles) | 3 | 3 | 3 | 4 | 3.25 |
| 4 (without washing) | 0 | 0 | 1 | 0 | 0.25 |
| 4a (1 washing cycle) | 0 | 0 | 0 | 1 | 0.25 |
| 4b (2 washing cycles) | 0 | 0 | 0 | 0 | 0 |

The results obtained show that the stratum corneum treated with polymer 1 and irradiated with light (example 4) has the weakest sweat odor perceived by the panel. Thus, treatment of the stratum corneum with the polymer according to the invention and with exposure to light confers a good deodorant property.

Likewise, after 1 washing cycle and 2 washing cycles, ythe stratum corneum treated with polymer 1 has the weakest sweat odor perceived by the panel. The treatment according to the invention thus confers a deodorant action that is very water resistant.

The deodorant effect of polymers 2 to 5 was also evaluated according to the protocol of example 4 using, respectively, compositions 4 to 7 (examples 5 to 8 respectively); the deodorant evaluations were recorded after 2 washing cycles.

The following results were obtained:

| example | Control evaluation A | Control evaluation B | Control evaluation C | Control evaluation D | mean |
|---|---|---|---|---|---|
| 5 (Polymer 2) (2 washing cycles) | 1 | 2 | 2 | 2 | 1.75 |
| 6 (Polymer 3) (2 washing cycles) | 1 | 0 | 0 | 0 | 0.25 |
| 7 (Polymer 4) (2 washing cycles) | 1 | 2 | 0 | 0 | 0.75 |
| 8 (Polymer 5) (2 washing cycles) | 1 | 0 | 1 | 1 | 0.75 |

The results obtained show that the stratum corneum treated with polymers 2 to 5 and irradiated with light have a weak sweat odor perceived by the panel.

EXAMPLE 9

A deodorant having the following composition is prepared:

| | |
|---|---|
| polymer of example 1 | 1 g |
| hydroxyethylcellulose (Natrosol ® 250 HHR CS from Ashland) | 0.2 g |
| Preserving agents | qs |
| Water qs | 100 g |

The composition obtained is applied to the skin of the underarms and the surface of the treated skin is then irradiated with white light (Lite-Pad lamp from the company Reicorp) for 5 minutes.

The composition applied under the arms makes it possible to reduce the odors due to perspiration.

EXAMPLE 10

A deodorant having the following composition is prepared:

| | |
|---|---|
| polymer of example 2 | 10 g |
| hydroxyethylcellulose (Natrosol ® 250 HHR CS from Ashland) | 0.3 g |
| Preserving agents | qs |
| Water qs | 100 g |

The composition obtained is applied to the skin of the underarms and the surface of the treated skin is then irradiated with blue light (goLITE BLU from the company Philips) for 5 minutes.

The composition applied under the arms makes it possible to reduce the odors due to perspiration.

EXAMPLE 11

A deodorant having the following composition is prepared:

| | |
|---|---|
| polymer of example 3 | 5 g |
| hydroxyethylcellulose (Natrosol ® 250 HHR CS from Ashland) | 0.2 g |
| Preserving agents | qs |
| Water qs | 100 g |

The composition obtained is applied to the skin of the underarms and the surface of the treated skin is then irradiated with blue light (Camag Box 3 lamp from the company Camag) for 1 minute.

A similar composition is prepared using polymer 4 or polymer 5 in place of polymer 3.

The composition applied under the arms makes it possible to reduce the odors due to perspiration.

EXAMPLE 12

A deodorant composition below is prepared:

| | |
|---|---|
| polymer of example 3 | 5 g |
| Preserving agents | qs |
| Water qs | 100 g |

The composition obtained is applied to the cork soles from the company Sunbed (reference 550), it is left to dry at ambient temperature (25° C.) for 30 minutes and then the surface of the soles is irradiated with blue light (Camag Box 3 lamp from the company Camag) for 1 minute.

The sole thus treated, placed in shoes, makes it possible to reduce foot odors.

EXAMPLE 13

A deodorant composition below is prepared:

| | |
|---|---|
| polymer of example 2 | 5 g |
| Preserving agents | qs |
| Water qs | 100 g |

A piece of cotton (5 cm×4 cm) (sold by the company SDC Enterprises Ltd, UK; reference 1205) was soaked in the composition obtained for 3 minutes and was then left to dry at ambient temperature (25° C.) for 30 minutes. The surface of the cotton was then irradiated with blue light (Camag Box 3 lamp from the company Camag) for 6 minutes (with the piece of wool being turned over after 3 minutes). The composition applied to the cotton makes it possible to reduce the odors.

It is thus possible to treat a piece of cotton fabric of greater size so as to then, after treatment, produce a piece of clothing such as a T-shirt. The person dressed in such a T-shirt can thus deodorize the body during the day.

The invention claimed is:

1. A cosmetic process for treating human body odor and optionally human perspiration, comprising:

(i) a step consisting in applying to the skin a cosmetic composition, comprising, in a physiologically acceptable medium, a chitosan polymer in which the amino groups are grafted with photoactive groups of azide or diazirine type of formula (I):

$$\text{(I)}$$

wherein R' independently represents H or an acetyl group or a group —CO-L-X, the polymer containing at least one group R'=—CO-L-X, L being a linear, branched or cyclic, saturated or unsaturated divalent hydrocarbon-based group comprising from 1 to 20 carbon atoms which may be interrupted with one or more non-adjacent heteroatoms chosen from sulfur, oxygen, or —NH—, —CO—, —CONH—, —COO—, —O—CO—N(Ra) groups, said divalent group optionally being substituted with one or more groups chosen from hydroxyl, amine, carboxylic acid, amide, cyano and ($C_1$-$C_4$)acylamino groups, with Ra, Rb and Rc independently denoting a hydrogen atom or a linear or branched;

X denotes a photoactive group of azide or diazirine type;

n ranges from 5 to 2000; and (ii) a step comprising exposing the skin to light radiation.

2. The process as claimed in claim 1, wherein the grafted chitosan (I) has a molar degree of grafting with photoactive groups —CO-L-X ranging from 0.1% to 50%.

3. The process as claimed in claim 1, wherein L is a linear, branched or cyclic, saturated or unsaturated (including aromatic) $C_1$-$C_{20}$ divalent hydrocarbon-based group which may be interrupted with one or more non-adjacent heteroatoms chosen from oxygen or with one or more non-adjacent groups chosen from —NH—, —CO—, —O—CO — and —NH—CO—.

4. The process as claimed in claim 1, wherein the grafted chitosan (I) has a degree of acetylation (—CO—$CH_3$) ranging from 0% to 50%.

5. The process as claimed in claim 1, wherein n ranges from 5 and 280.

6. The process as claimed in claim 1, wherein the grafted chitosan polymer is of formula (Ia):

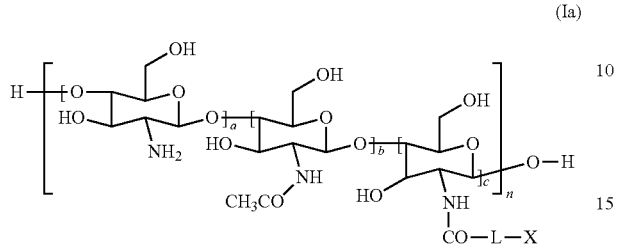

(Ia)

wherein the grafted chitosan comprises a units bearing a free amino group, b units bearing an N-acetyl amino group and c units bearing an amino group grafted with a photoactive group —CO-L-X;

b ranges from 0 to 0.5;

c ranges from 0.001 to 0.5;

and a+b+c=1.

7. The process as claimed in claim 1, wherein L is chosen from the following groups:

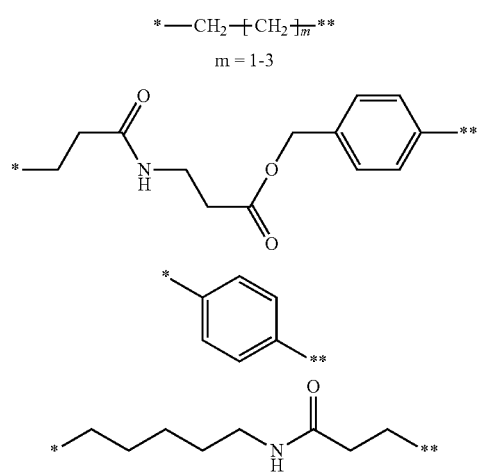

* representing the bond with the group C(O);

** representing the bond with the photoactive group X.

8. The process as claimed in claim 1, wherein photoactive group X is chosen from the following groups:

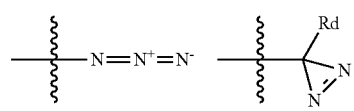

with Rd denoting H or a linear or branched $C_1$-$C_6$ alkyl radical, or a $CF_3$ radical.

9. The process as claimed in claim 1, wherein the group —CO-L-X is chosen from:

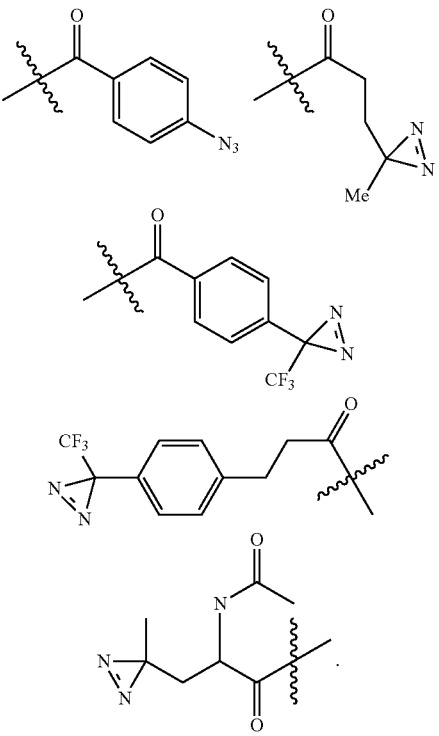

10. The process as claimed in claim 1, wherein the grafted chitosan (I) or (Ia) is present in the composition in a content ranging from 0.1% to 10% by weight, relative to the total weight of the composition.

11. The process as claimed in claim 1, wherein the step comprising applying light radiation is performed after or at the same time as (simultaneously with) the step comprising applying the cosmetic composition comprising the grafted chitosan (I).

12. The process as claimed in claim 1, wherein step (ii) comprising applying light radiation is performed after step (i) comprising applying the cosmetic composition comprising the grafted chitosan (I).

13. The process as claimed in claim 1, wherein the light radiation is natural light or artificial light with a wavelength of between 360 and 600 nm.

14. The process as claimed in claim 1, in which the light radiation has a source chosen from arc lamps; fluorescent lamps; incandescent lamps; LEDs and lasers.

15. The process as claimed in claim 1, in which the exposure time to the light radiation is at least 5 seconds.

16. A polymer of formula (II):

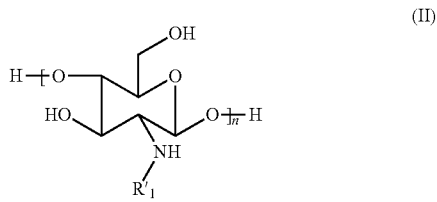

(II)

wherein $R'_1$ independently represents H or an acetyl group or a group —CO-L-X of formula (c) below:

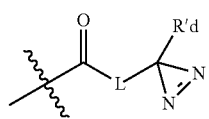

(c)

wherein:
L being a linear, branched or cyclic, saturated or unsaturated divalent hydrocarbon-based group comprising from 1 to 20 carbon atoms which may be interrupted with one or more non-adjacent heteroatoms chosen from sulfur, oxygen, or —NH—, —CO—, —CONH—, —COO—, —O—CO—N(Ra)—, said divalent group optionally being substituted with one or more groups chosen from hydroxyl, amine, carboxylic acid, amide, cyano and (C$_1$-C$_4$)acylamino groups, with Ra, Rb and Rc independently denoting a hydrogen atom or a linear or branched C$_1$-C$_6$ alkyl radical;
R'd denotes H or a linear or branched C$_1$-C$_4$ alkyl radical, or a CF$_3$ radical;
the polymer containing at least one group —CO-L-X of formula (c),
n ranges from 5 to 1700.

17. The polymer as claimed in claim 16, wherein the grafted chitosan (I) has a molar degree of grafting with photoactive groups —CO-L-X ranging from 0.1% to 50%.

18. The polymer as claimed in claim 16, wherein the grafted chitosan (I) has a degree of acetylation (—CO—CH$_3$) ranging from 0% to 50%.

19. The polymer as claimed in claim 16, wherein it is of formula (II'):

(II')

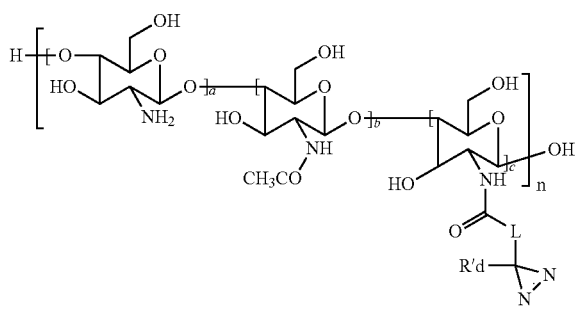

wherein
b ranges from 0 to 0.5;
c ranges from 0.001 to 0.5;
and a+b+c=1.

20. The polymer as claimed in claim 16, wherein the grafted chitosan polymer (II) is of formula (IIa):

(IIa)

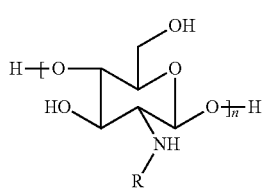

wherein R denotes H or acetyl or a group (J):

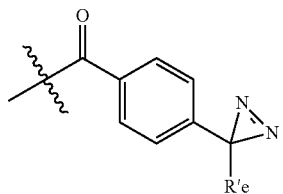

wherein R'e=CH$_3$ ou CF$_3$, the polymer comprising at least one group (J);
or of formula (IIb)

(IIb)

wherein R denotes H or acetyl or a group (K):

with p=1 to 3, the polymer comprising at least one group (K).

21. A composition comprising, in a physiologically acceptable medium, a polymer (II) or (II') or (IIa) or (IIb) as claimed in claim 16.

22. The composition as claimed in claim 21, wherein polymer (II) or (IIa) or (IIb) is present in a content ranging from 0.1% to 10% by weight, relative to the total weight of the composition.

23. The composition as claimed in claim 1, which comprises a cosmetic adjuvant chosen from water, emulsifiers, preserving agents, sequestrants, fragrances, thickeners, oils, waxes and film-forming polymers.

24. A process for deodorizing feet and/or shoes, comprising placing in a shoe a sole of which the surface has been treated by applying to said surface a composition comprising a grafted chitosan in which the amino groups are grafted with photoactive groups of azide or diazirine type of formula (I):

(I)

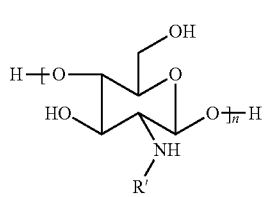

wherein R' independently represents H or an acetyl group or a group —CO-L-X, the polymer containing at least one group R'=—CO-L-X, L being a linear, branched or cyclic, saturated or unsaturated divalent hydrocarbon-based group comprising from 1 to 20 carbon atoms which may be interrupted with one or more non-adjacent heteroatoms chosen from sulfur, oxygen, or —NH—, —CO—, —CONH—, —COO—, —O—CO—N(Ra)— groups, said divalent group optionally being substituted with one or more groups chosen from hydroxyl, amine, carboxylic acid, amide, cyano and $(C_1$-$C_4)$acylamino groups, with Ra, Rb and Rc independently denoting a hydrogen atom or a linear or branched;

X denotes a photoactive group of azide or diazirine type;

n ranges from 5 to 2000; and then exposing the treated surface to light radiation.

25. A process for deodorizing a body (or part of the body), comprising clothing the body (or part of the body) with clothing made of textile fabric of which the surface has been treated by applying to the surface of the textile a composition comprising a grafted chitosan in which the amino groups are grafted with photoactive groups of azide or diazirine type of formula (I):

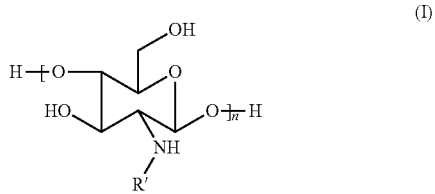

(I)

wherein R' independently represents H or an acetyl group or a group —CO-L-X, the polymer containing at least one group R'=—CO-L-X, L being a linear, branched or cyclic, saturated or unsaturated divalent hydrocarbon-based group comprising from 1 to 20 carbon atoms which may be interrupted with one or more non-adjacent heteroatoms chosen from sulfur, oxygen, or —NH—, —CO—, —CONH—, —COO—, —O—CO—N(Ra)— groups, said divalent group optionally being substituted with one or more groups chosen from hydroxyl, amine, carboxylic acid, amide, cyano and $(C_1$-$C_4)$acylamino groups, with Ra, Rb and Rc independently denoting a hydrogen atom or a linear or branched;

X denotes a photoactive group of azide or diazirine type;

n ranges from 5 to 2000; and then exposing the treated surface to light radiation.

26. The process as claimed in claim 25, wherein the part of the body is the feet and the item of textile clothing is chosen from socks, stockings and tights.

27. A process for deodorizing feet comprising clothing the feet with an item of clothing for the feet made of textile fabric treated by applying to said textile fabric a composition comprising a grafted chitosan in which the amino groups are grafted with photoactive groups of azide or diazirine type of formula (I):

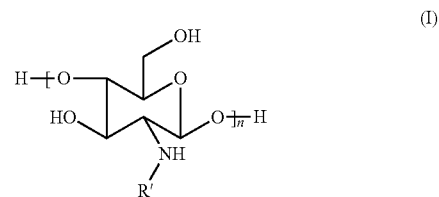

(I)

wherein R' independently represents H or an acetyl group or a group —CO-L-X, the polymer containing at least one group R'=—CO-L-X, L being a linear, branched or cyclic, saturated or unsaturated divalent hydrocarbon-based group comprising from 1 to 20 carbon atoms which may be interrupted with one or more non-adjacent heteroatoms chosen from sulfur, oxygen, or —NH—, —CO—, —CONH—, —COO—, —O—CO—N(Ra)— groups, said divalent group optionally being substituted with one or more groups chosen from hydroxyl, amine, carboxylic acid, amide, cyano and $(C_1$-$C_4)$acylamino groups, with Ra, Rb and Rc independently denoting a hydrogen atom or a linear or branched;

X denotes a photoactive group of azide or diazirine type;

n ranges from 5 to 2000; and then exposing the treated textile fabric to light radiation.

* * * * *